(12) United States Patent
Legrand et al.

(10) Patent No.: US 6,899,872 B1
(45) Date of Patent: May 31, 2005

(54) ABSORBABLE DIETARY COMPOSITION FOR IMPROVING THE BIOLOGICAL BALANCE OF INTESTINAL TRACT FLORA

(76) Inventors: Charles Legrand, 24 Avenue de Creully, Ombrages No. 3, Caen (FR), F-14000; Edmond Roussel, 16 rue Saint Loup, Avenay (FR), F-14210

( * ) Notice: Subject to any disclaimer, the term of this patent is extended or adjusted under 35 U.S.C. 154(b) by 0 days.

(21) Appl. No.: 10/077,240

(22) Filed: Feb. 15, 2002

Related U.S. Application Data

(63) Continuation of application No. 09/574,369, filed on May 19, 2000, now abandoned, which is a continuation of application No. 09/077,272, filed on Aug. 7, 1998, now abandoned, which is a continuation of application No. PCT/PR96/01871, filed on Nov. 26, 1996.

(30) Foreign Application Priority Data

Nov. 27, 1995 (FR) .............................. 95 14019

(51) Int. Cl.$^7$ .......................... A01N 63/00; A61K 9/48; A61K 9/20; A61K 9/14
(52) U.S. Cl. ..................... 424/93.4; 424/93.3; 424/451; 424/464; 424/489
(58) Field of Search .............................. 424/93.3–93.48, 424/451, 464, 489

(56) References Cited

U.S. PATENT DOCUMENTS

| | | | | |
|---|---|---|---|---|
| 5,478,557 A | * | 12/1995 | Nisbet et al. | 424/93.21 |
| 5,501,857 A | * | 3/1996 | Zimmer | 424/438 |
| 5,529,793 A | * | 6/1996 | Garner et al. | 426/61 |
| 5,639,659 A | * | 6/1997 | Barefoot et al. | 435/252.1 |
| 5,716,615 A | * | 2/1998 | Cavaliere et al. | 424/93.4 |

\* cited by examiner

*Primary Examiner*—Shengjun Wang
(74) *Attorney, Agent, or Firm*—Robert B. Hughes; Hughes Law Firm, PLLC

(57) ABSTRACT

A method for improving the biological equilibrium of intestinal tract flora in humans and other mammals, the purpose of this being to decrease emission of the malodorous gases from the humans and other mammals. The method comprises ingesting an effective quantity of a dehydrated composition comprising propionic bacteria in an amount of at least $10^9$ cells per gram of the composition. In a preferred form, the composition contains about 80 to 90 parts propionic bacteria to about 20 to 1 parts bifid bacteria.

14 Claims, No Drawings

ABSORBABLE DIETARY COMPOSITION FOR IMPROVING THE BIOLOGICAL BALANCE OF INTESTINAL TRACT FLORA

RELATED APPLICATIONS

This application is a continuation of patent application of U.S. Ser. No. 09/574,369, filed May 19, 2000, now abandoned, which is a continuation patent application of U.S. Ser. No. 09/077,272, filed Aug. 7, 1998, now abandoned which is a continuation of PCT/PR/96/01871 filed Nov. 26, 1996, which is a continuation of FRENCH 9514019, filed Nov. 27, 1995.

This invention relates to an absorbable dietary composition for improving the biological equilibrium of intestinal tract flora in humans and mammals.

It is well known that the content of the human alimentary canal, corresponding to approx. 1 to 1.5 kg of nutritional material in the process of being digested, contains a large population of microorganisms which can be estimated at around $10^{10}$ cells per gram in the colon.

This population in divided into different bacterial groups, some of which are innocent or beneficial, whereas others, particularly coliforms and putrefying bacteria, lead to the production of toxic substances and have an adverse influence on health.

There have been various studies, notably since the beginning of the twentieth century, which have attempted to demonstrate that the presence of a large population of lactobacilli very severely limits the development of the putrefying genera and consequently the production of these toxic materials.

The idea has therefore quite naturally been put forward of introducing a large population of these bacteria into the body, either by way of a particular food or by direct ingestion of these microbial cells; among the possible lactic flora, it has notably been recommended that the following bacteria be absorbed: *Lactobacillus bulgaricus, Lactobacillus acidophilus* or even *Streptococcus faecium* (those are mentioned by way of example only and are not intended to be exhaustive).

However, administering these bacteria has tot led to the expected results, taking account of the fact that, on the one hand, the microbe population of the intestinal tract constitutes a mass whose equilibrium it is difficult to alter radically on a long-term basis and, on the other hand, that it has been possible to establish that consuming lactobacilli has little influence on the putrefactive flora which causes the known ailments and upsets.

More recently, that is to say during the seventies, the idea was put forward of introducing into the human diet non-lactic genera of the bifid type, which, as has been shown, are capable of promoting good health. Ferments of this sort may be consumed either by way of milky puddings or other dairy products fermented in part by a bifid flora, or else via the direct ingestion of live cells in a suitable presentation form.

Introducing the bacteria in this way has, however, proved disappointing in practice, particularly taking account of the fact that it is very difficult to successfully implant the exogenous bifid bacteria on a long-term basis in the human intestine, particularly in subjects whose intestinal equilibrium is not as good as it might be.

Proceeding from the background of these general findings, the idea underlying the invention was to search for a means whereby the bifid population could be increased.

In doing so the present authors came across the work of Professor Henri Berrens in Lille, who was able to establish that propionic acid is a specific selective and elective element of the bifid flora.

It is known that this organic acid is one of the products that result from the fermentation notably of the lactate by a particular type of bacteria, the propionic bacteria which, whilst they do not belong to the lactobacilli, have nevertheless been present in the human diet for centuries, in particular given that it is these bacteria which make it possible to obtain the holes when producing the cheese known as 'Emmental': this is because, at the end of the process, these cheeses contain around $10^9$ cells/g of propionic bacteria.

It should be noted that, apart from propionic acid, the fermentation of propionic bacteria produces, enter alia, acetic acid and carbon dioxide.

In parallel with this work, it was established thanks to the publication by Tsutomu Kaneko, Hiroharu Mori, Megumi Iwata and Sachiki Meguro, "Growth Stimulator for Bidifobacteria Produced by *Propionibacterium freudenreichii* and Several Intestinal Bacteria", 1994, J. Dairy Sci. 77:393–404, on the one hand that propionic bacteria, notably bacteria of the type *Propionibacterium freudenreichii*, can produce a bifid bacteria growth factor and, on the other hand, that the short-chain fatty acids, and in particular propionic acid, have a very pronounced inhibiting action on the growth of many undesirable intestinal bacteria but stimulate the growth of bifid bacteria.

It has likewise already been proposed, under JP-A-07 227 207, to add propionic bacteria to foodstuffs, notably to fermented milk containing bifid bacteria, with the aim of increasing the survival rate of these bacteria.

It should, moreover, be noted that from U.S. Pat. No. 4,806,3689 there is known a dietary tablet based on nutritional fibres, especially apple fibres which may contain bifid bacteria, and, furthermore, a lesser quantity of propionic bacteria acting as an anti-fungal agent.

It was on the basis of these preliminary findings that the idea according to the invention suggested itself, namely to look for a way of directly consuming large quantities of combined bifid and propionic ferments within the limits of a measured presentation that can be readily ingested.

It was realised that such a mode of absorption is beneficial from every aspect and in particular makes it possible to significantly reduce the usual harmful incidences of putrefactive bacteria, even though the reverse effect was to be expected, taking into account the large amount of carbon dioxide released following propionic fermentation, as witnessed by the part played by these ferments in opening up the holes in cheeses.

Consequently it is the object of this invention to provide an absorbable dietary composition for improving the biological equilibrium of intestinal tract flora in humans and mammals, characterised by the fact that it is constituted by a dehydrated preparation containing propionic bacteria and bifid bacteria in an amount of at least $10^9$ cells per gram, and preferably in the order of $10^{10}$ to $10^{12}$ cells per gram, which means that it is highly concentrated in bacteria.

Generally speaking, these bacteria will be live, but they may also be killed, on condition that care has been taken not to destroy their enzyme content.

These bacteria are preferably distributed as 80 to 99% propionic bacteria and 20 to 1% bifid bacteria.

The composition in accordance with the invention therefore advantageously contains on average ten times as many propionic bacteria as bifid bacteria.

The bifid bacteria employed belong, as a general rule, to the genus *Bifidobacterium* and are preferably chosen from the strains *B. bifidum, B. longum, B. adolescentis, B. breve, B. infantis* and *B. pseudolongum*.

The propionic bacteria belong, likewise as a general rule, to the genera *Propionibacterium freudenreichii* or *Propionibacterium shermanii* or *Propionibacterium thoenii* or *Propionibacterium jensenii* or *Propionibacterium acidipropionici*.

These bacteria may be employed as a pure strain or, in preference, as a mixture of strains; in the case of the propionic bacteria it is advantageous to simultaneously combine highly autolytic strains and not very autolytic strains.

The invention likewise concerns the use of a dehydrated preparation containing propionic bacteria in an amount of at least $10^9$ cells per gram, preferably in the order of $10^{10}$ to $10^{12}$ cells per gram, to obtain an absorbable dietary composition for improving the biological equilibrium of the intestinal tract flora in humans and mammals and in particular for increasing the bifid population.

It should be noted that this bifid population may originate either from endogenous bacteria or from exogenous bacteria added to the preparation.

This composition is preferably presented in the form of individual fractions of around 100 mg to 1 g, preferably 200 to 500 mg, containing the dose of bacteria that needs to be absorbed daily.

These fractions may be ingested directly or first be diluted in a liquid; they may be conditioned in any form that facilitates absorption: tablets, sachets of granulated or ungranulated powder, etc.

It has been verified that such concentrated dehydrated preparations of propionic bacteria conserved for two years at +4° C. experience a fall in concentration of less than a Napierian logarithm.

Experience has proved that capsules, either gastro-resistant or otherwise, are a particularly advantageous form of presentation.

According to another feature of the invention, each individual fraction contains at least $10^9$ bacteria and preferably in the order of $10^{10}$ to $10^{12}$ bacteria.

It should be noted that on this side of the threshold of $10^9$ bacteria the effect is random, which in all probability is due to the fact that the bacteria are then destroyed by the stomach's acidity or by the bile salts before they reach the colon.

In accordance with the invention it is therefore proposed that each human subject should absorb daily, by way of a food supplement, a dose of propionic bacteria flora of the alimentary canal (representing around $10^{14}$ units), which is a distinctly higher quantity than has previously been proposed for other types of bacteria.

It has been verified that such a dosage in accordance with the invention produces no harmful effects and brings about, over and above the aforementioned advantages:

a notable decrease in the emission of malodorous gases typical of putrefying bacteria;

a change in stool colour and odour.

These findings are clearly of a kind to throw light on the "symbiotic" action of the propionic bacteria and the bifid bacteria, with the propionic bacteria stimulating the development of the bifids.

This result was confirmed by a study carried out with the aim of verifying whether strains of *Propionibacterium* were able to either improve the rate at which a strain of *Bifidobacterium bifidum* established itself in the alimentary canal of mice, or to increase its level of activity in the various segments of the alimentary canal.

In an initial phase, this study showed that it is not possible to establish *Propionibacterium* on a long-term basis in the alimentary canal of mice, even germ-free mice, that is to say in the absence of digestive flora.

Conversely, it was shown that the addition of *Propionibacterium* in culture to the drinking water of these mice makes it possible to stimulate the rate at which strains of *Bifidobacterium bifidum* colonise the alimentary canal.

This scientific study therefore provides the proof that a genuine synergy exists between the actions of the propionic bacteria and of the bifid bacteria.

Moreover, these results have been verified by a series of investigations carried out, on the one hand, in vivo in healthy human subjects and, on the other hand, in vitro.

In vivo Investigations

The object of these investigations was to study, in the hospital environment of the CHU (University Hospital) at Caen in France, the survival and/or colonisation of strains of propionic bacteria in the intestinal environment, and their effect on the bifid flora of a set of nineteen healthy male voluntary subjects.

This study involved each volunteer ingesting, every day for two weeks, a capsule containing 5 $10^{10}$ propionic bacteria selected by INRA (Institut national de la recherche agronomique=French agronomical research institute) and taken from a bank of strains used in the cheese industry, which therefore means that they are completely harmless to humans.

The propionic bacteria administered were divided into two strains of approximately 50% each, one of these strains being not very autolytic whilst the other became autolytic in the stomach and at the start of the small intestine under the action of the bile salts.

The study of the faecal flora was carried out on a stool specimen prior to administering propionic bacteria in order to obtain the basal status of the flora, during said administration and subsequent thereto, in order to assess how long the exogenous bacteria were able to survive in the alimentary canal of the voluntary subjects.

This study included a count of the ingested propionic bacteria and of the bifidobacteria.

Following on from these investigations it was verified that the population of propionic bacteria in the stools increased significantly with the first sampling whilst the subjects were taking propionic bacteria, but that this effect is transitory and ceases a short time after ingestion of the bacteria stops.

These results show that a fraction of the propionic bacterial strains is able to survive in the human alimentary canal, but that they are unable to colonise it in the long term.

To assess the effect of the propionic bacteria on the bifid population, attention was also given to the samplings undertaken (a) prior to ingestion of the propionic bacteria; (b) during said ingestion; and thereafter (two samplings (c and d) performed one week apart).

It should be noted that sampling (b) is the mean of two samplings performed one week apart.

A count of the Bifidobacteria made it possible to calculate the means (in Napierian logarithms) of the populations during these four periods.

Accordingly, respective mean values were found of (a) 8:40; (b) 8.90; (c) 9.43; and (d) 8.89. The evolution over time was studied using a non-parametric statistical test for matched populations, the Wilcox matched-paired signed-ranks test. It shows that during the ingestion of propionic bacteria (sampling b) the bifid population increases significantly with respect to the base figure (sampling a) (p=0.0096) and remains high at the first check (sampling c) after their ingestion ceases (p=0.031). There is no difference between the Bifidobacterial count during the administration of propionic bacteria (sampling b) and said first check after it ceases (1 week) (sampling c) (p=0.19); the population of Bifidobacteria decreases at the second check (sampling d) (p=0.49) in comparison to the first check after cessation (sampling c) and returns to the level prior to the administration of the propionic bacteria (sampling a) (p=0.25) between the second check (sampling d) and the sampling preceding it (sampling c).

These results show that administering high doses of propionic bacteria promotes the development of the bifid flora; this effect is rapid, observed from the very first week and persisting for at least one week after ingestion of the propionic bacteria stops.

In vitro Investigations

The object of these investigations was:
 to study the resistance of the propionic bacteria to digestive "stress", i.e. the stomach's acidity and bile salts,
 to study what effect cultures of propionic bacteria have on the growth of the bifidobacteria,
 to identify, if applicable, the agent responsible for this effect.

Resistance of Propionic Bacteria to Digestive "Stress"

Between the time when they are ingested and the time when they arrive in the colon where they come into contact with the intestinal bacteria, notably the bifid bacteria, the propionic bacteria are subjected to a number of "stresses" unfavourable to their survival, chief of which are the stomach's acidity and contact with the bile salts in the small intestine.

To assess how resistant the propionic bacteria are to these "stresses", two strains belonging to the genus *Propionibacterium freudenreichii* were chosen, viz. strain LS 410 which is not very autolytic and strain LS 2501 which is highly autolytic.

In humans the pH of the stomach, following the arrival of a food bolus, is between 2 and 3, and the average time taken to empty the stomach is in the order of 90 minutes.

In order to evaluate the resistance of the aforementioned strains to stomach acidity, said strains were therefore tested at different pH levels (2, 3 and 4) for 90 minutes at 37° C.

The following observations were made:
 At pH 4, the viability of the two strains is totally unadulterated;
 At pH 3, strain LS 410 is undamaged but strain LS 2501 exhibits a slight fall in viability;
 At pH 2, virtually the entirety of the two strains dies after 90 minutes of incubation.

The resistance of the two strains to bile salts at 37° C. was evaluated by choosing bile acid concentrations of 1, 2 and 5 g/l, which is essentially the concentration at the entrance to the small intestine.

Thanks to these investigations it was found that at the weakest concentration (1 g/l) strain LS 410 remains totally resistant even after 5½ hours incubation time. Conversely, strain LS 2501 exhibits less resistance.

In the presence of 2 to 5 g/l bile acids, the viability of the two strains falls off sharply, with strain LS 2501 being more sensitive than strain LS 410.

In conclusion, these investigations showed that the two strains studied exhibit great resistance in the face of moderate digestive "stresses". However, the majority of the bacteria are unable to resist conditions of extreme "stress", with the highly autolytic strain (LS 2501) being the more sensitive.

These results demonstrate the necessity, in order to obtain a noteworthy effect on the biological equilibrium of the intestinal tract flora in humans, of ingesting a large quantity of bacteria in order to ensure adequate survival of the strains at the entrance to the colon.

Influence of Propionic Bacterial Cultures on Bifidobacterial Growth

To carry out these investigations, two strains of bifid bacteria, *B. longum* and *B. bifidum*, were seeded in a medium containing, in half-and-half proportions:
 a culture broth suitable for growing bifid bacteria,
 a culture of propionic bacteria (strains LS 410 or LS 2501), either young (48 hrs) and hence relatively unlysed, or else 11 days old and hence highly lysed, notably as regards the autolytic strain LS 2501.

Accordingly it was observed that the presence of a young culture of LS 410 and, to a lesser extent, of LS 2501, results in a higher level of the total population of *B. bifidum* at the end of the exponential phase: the number of viable bacteria is 3 to 4 times greater in the presence of LS 410 and 2 to 3 times greater in the presence of LS 2501.

With regard to *B. longum*, the LS 410 culture results, at the end of growth, in twice as high a population of *B. longum*.

In the case of the aged cultures, a markedly favourable effect by the two strains was observed on the growth of *B. bifidum* during the exponential phase (population 2 or 3 times greater).

In conclusion, the two propionic bacteria tested in this study have an influence on the growth of *B. bifidum*. Their effect varies with the age of the culture: young cultures bring about an increase in the viability of the bifids at the end of growth which results in final populations 2 to 4 times greater (a more marked effect in LS 410), whereas aged cultures exert an action solely at the start of growth by reducing the time taken for generation, but without altering final population levels.

Identifying the Agent Responsible for the Bifidogenous Effect

The influence of propionic bacterial culture swim-ups

The role of propionic acid.

Experiments were carried out similar to those mentioned above, in the first place using only the culture swim-ups making up the extracellular fraction of the bacteria, and in the second place using a comparative medium supplemented with propionic acid.

It was accordingly observed that, compared to a control, the propionic bacterial culture swim-ups have a markedly stimulating effect on the growth of *B. bifidum* (3 to 4 times more viable bacteria after 9 hours in culture); this effect is more pronounced at the end of growth with the LS 2501 strain.

It was verified that these stimulating effects are due in part to the influence of the propionate. Nevertheless it appears that the propionate is not solely responsible for these effects, notably in the case of the LS 2501 strain.

Propionic acid likewise has a stimulating effect on the metabolic activity of *B. longum*.

Influence of the Intracellular Medium:

It was observed that the presence of the intracellular medium of the two strains of propionic bacteria brings about a sizeable increase in the optical density and the cellular dry weight of the two bifids. However, these effects do not correlate with an increase in the growth of *B. bifidum* or *B. longum* given that both their viability and their metabolic activity at the time of growth are not altered.

Influence of Insulated Walls:

It was observed that the insulated walls of propionic bacteria, whether or not hydrolysed, have no influence on the growth of *B. longum* and *B. bifidum*.

In conclusion, the promoter effect of the propionic bacteria on the growth of the bifids does not appear to be linked either to their intracellular content or to the walls. Conversely, the compounds responsible are chiefly localised in the intracellular medium. The propionate is compounds.

We claim:

1. A method of decreasing emissions of malodorous gas from humans and mammals which are in need of such treatment by stimulating the development of bifid bacteria in the intestinal tract., said method comprising ingesting in said humans and other mammals an effective quantity of a dehydrated composition comprising propionic bacteria in an amount of at least $10^9$ cells per gram of said composition to accomplish the stimulation of bifid bacteria in the intestinal tract.

2. The method as in claim 1, wherein the amount of propionic bacteria is at approximately $10^{10}$ cells per gram of said composition.

3. The method as recited in claim 1 wherein said amount is up to about $10^{12}$ cell per gram of said composition.

4. The method as claimed in claim 1, where in the composition further comprises bifid bacteria.

5. The method as claimed in claim 4, wherein the composition contains about 80 to 90 parts propionic bacteria to about 20 to 1 parts bifid bacteria.

6. The method as claimed in claim 5, wherein the propionic bacteria belong to genus *Propionibacterium freudenreichii* or *Propionibacterium acidpropionici* or combinations thereof.

7. The method as recited in claim 1, wherein the propionic bacteria belong to genus *Propionibacterium freudenreichii* or *Propionibacterium shermanil* or *Propionibacterium jensenii* or *Propionibacterium acidipropionici* or combinations thereof.

8. The method as claimed in claim 6, wherein the bifid bacteria belong to the genus *Bifidobacterium* and are chosen from the branches *B. bifidium, B. longum, B. adolescentis, B. breve, B. infantis* and *B. pseudolongum*, or combinations there of.

9. The method as claimed in claim 4, wherein the composition is presented in the form of individual fractions of approximately 100 mg to 1 g, containing the dose of bacteria that is absorbed daily.

10. The method as recited in claim 9, wherein the individual fractions are approximately 300 to 500 mg.

11. The method as claimed in claim 9, wherein the composition is provided in the form of capsules, tablets, or sachets of granulated or ungranulated powder.

12. The method as claimed in claim 9, wherein each individual fraction contains at least $10^9$.

13. The method as recited in claim 9, wherein each individual fraction contains at least $10^{10}$ bacteria.

14. The method as recited in claim 13, wherein each individual fraction contains no more than $10^{12}$ bacteria.

* * * * *

UNITED STATES PATENT AND TRADEMARK OFFICE
CERTIFICATE OF CORRECTION

PATENT NO. : 6,899,872 B1  
APPLICATION NO. : 10/077240  
DATED : May 31, 2005  
INVENTOR(S) : Charles Legrand and Edmond Roussel Page 1 of 1

It is certified that error appears in the above-identified patent and that said Letters Patent is hereby corrected as shown below:

on title page, item [73] insert the following:  
Assignee: LABORATOIRES STANDA, S.A., 68 rue Robert-Kaskoreff, F-14050, Caen Cedex, FRANCE Signed and Sealed this Fifth Day of September, 2006

JON W. DUDAS  
*Director of the United States Patent and Trademark Office*